US012797049B2

(12) United States Patent
Liao et al.

(10) Patent No.: US 12,797,049 B2
(45) Date of Patent: Nov. 17, 2026

(54) SAMPLE COLLECTION DEVICE

(71) Applicant: Quanta Vision Co., Ltd., New Taipei City (TV)

(72) Inventors: Kuan-Chiao Liao, New Taipei City (TW); Ya-Chieh Yu, New Taipei City (TW); Da-Li Wang, New Taipei City (TW)

(73) Assignee: QUANTA VISION CO., LTD., New Taipei City (TW)

( * ) Notice: Subject to any disclaimer, the term of this patent is extended or adjusted under 35 U.S.C. 154(b) by 421 days.

(21) Appl. No.: 18/414,982

(22) Filed: Jan. 17, 2024

(65) Prior Publication Data

US 2025/0228533 A1 Jul. 17, 2025

(51) Int. Cl.
*A61B 10/00* (2006.01)

(52) U.S. Cl.
CPC ...... *A61B 10/0051* (2013.01); *A61B 10/0096* (2013.01)

(58) Field of Classification Search
CPC ............ A61B 10/0045; A61B 10/0048; A61B 10/0051; A61B 10/0064; A61B 2010/0216; A61B 2010/0054; A61B 2010/0067; A61B 2010/0074; A61B 2010/008; G01N 1/02; G01N 1/10; G01N 2001/028
See application file for complete search history.

(56) References Cited

U.S. PATENT DOCUMENTS 4,418,702 A * 12/1983 Brown ............... A61B 10/0051 422/430
4,580,577 A * 4/1986 O'Brien ............. A61B 10/0051 422/430
5,084,245 A * 1/1992 Berke .............. G01N 33/54366 422/430
5,211,182 A * 5/1993 Deutsch ............. A61B 10/0012 600/584
7,666,667 B2 * 2/2010 Yong ..................... B01L 3/5029 435/309.1
7,927,562 B2 * 4/2011 Wan ......................... B01L 3/502 422/549
11,099,183 B2 * 8/2021 Lei ....................... G01N 33/946
(Continued)

FOREIGN PATENT DOCUMENTS

DE 102021115185 A1 * 12/2022 ......... A61B 10/0051
JP 2010038640 A * 2/2010 ............ C12M 33/02
(Continued)

*Primary Examiner* — Adam J Eiseman
(74) *Attorney, Agent, or Firm* — MUNCY, GEISSLER, OLDS & LOWE, P.C.

(57) ABSTRACT

A sample collection device is provided, wherein the sample collection device includes: a container including a chamber and a squeeze portion within the chamber, opposing ends of the container including an opening and an outlet, respectively, the opening and the outlet being in communication with the chamber; and a sampling unit including a main body, the main body including a sample collection member which is made of deformable absorbent material, and a sealing portion, the sample collection member being insertable into the chamber and radially urging the squeeze portion, the sealing portion being annularly and sealingly engaged with an inner wall of the chamber.

7 Claims, 6 Drawing Sheets

(56) References Cited

U.S. PATENT DOCUMENTS

| | | | | |
|---|---|---|---|---|
| 2003/0064526 | A1* | 4/2003 | Niedbala | B01L 3/5029 600/584 |
| 2004/0184954 | A1* | 9/2004 | Guo | B01L 3/5023 422/400 |
| 2004/0237674 | A1* | 12/2004 | Wu | B01L 3/5029 73/864 |
| 2005/0119589 | A1* | 6/2005 | Tung | B01L 3/5023 600/584 |
| 2006/0057027 | A1* | 3/2006 | Hudak | A61B 10/0051 422/549 |
| 2009/0024060 | A1* | 1/2009 | Darrigrand | A61B 10/0051 600/584 |
| 2009/0030342 | A1* | 1/2009 | Flanigan | B01L 3/5029 600/572 |
| 2012/0094303 | A1* | 4/2012 | Engel | A61B 10/0045 435/7.1 |
| 2016/0045187 | A1* | 2/2016 | Terbrueggen | B01L 3/5023 435/6.1 |
| 2018/0267030 | A1* | 9/2018 | Fiechtner | G01N 33/54306 |
| 2020/0100774 | A1* | 4/2020 | Lei | B01L 3/502 |
| 2020/0376483 | A1* | 12/2020 | Loudermilk | B01L 3/5023 |
| 2020/0383664 | A1* | 12/2020 | Loudermilk | B01L 3/5029 |
| 2021/0190767 | A1* | 6/2021 | Penagondla | A61B 10/0045 |
| 2021/0228191 | A1* | 7/2021 | Baek | A61B 10/0051 |
| 2021/0330300 | A1* | 10/2021 | Ling | A61B 5/150755 |
| 2022/0249073 | A1* | 8/2022 | Charlton | G01N 1/02 |
| 2023/0152188 | A1* | 5/2023 | Yu | G01N 1/14 73/864.72 |
| 2023/0293068 | A1* | 9/2023 | Haupt | A61B 10/0051 600/573 |

FOREIGN PATENT DOCUMENTS

| | | | | | |
|---|---|---|---|---|---|
| KR | 20220002829 | U | * | 12/2022 | A61B 10/0051 |
| WO | WO-2009050666 | A1 | * | 4/2009 | B01L 3/502715 |
| WO | WO-2018188458 | A1 | * | 10/2018 | B01L 3/5023 |
| WO | WO-2022158813 | A1 | * | 7/2022 | A61B 10/0045 |

* cited by examiner

SAMPLE COLLECTION DEVICE

BACKGROUND OF THE INVENTION

Field of the Invention

The present invention relates to a sample collection device, and particularly to a sample collection device for collecting and testing a specimen.

Description of the Prior Art

Many infectious rapid test devices generally collect specimens from oral cavity or nasal cavity for testing nowadays. The current specimen collection methods do not offer an accurate and effective way to quantify the specimen. Therefore, if quantitative analysis is required, additional quantitative experiments must be performed after specimen collection; however, this process is very complicated and inconvenient.

Furthermore, the proportion between the concentration of the specimen and the buffer solution in the rapid test reagent affects the result. Therefore, if accurate quantification cannot be achieved, it will inevitably lead to erroneous results.

The conventional rapid test devices include a sample-dropping rapid test device, a rapid test device with a volcano-shaped opening, a one-piece molded test device, and a squeezing machine. The sample-dropping rapid test device uses a dropper to drop the testing solution into the cassette; thus, it is difficult to quantify the testing solution due to the varying pressure applied while pressing the dropper. The rapid test device with a volcano-shaped opening is hard for user to control the squeezing pressure, resulting in poor quantification. It is impossible to quantity the testing solution by the one-piece molded test device, because a saliva sponge and a detection cassette of the one-piece molded test device are integrally formed. The squeezing machine uses a cassette to collect the saliva. The cassette containing saliva is then placed into the squeezing machine for compression. However, the squeezing machine has disadvantages in high equipment cost and large size; thus, it is unsuitable for portable.

The present invention is, therefore, arisen to obviate or at least mitigate the above-mentioned disadvantages.

SUMMARY OF THE INVENTION

The main object of the present invention is to provide a sample collection device which provides sampling and quantification of specimens.

To achieve the above and other objects, a sample collection device is provided, wherein the sample collection device includes: a container including a chamber and a squeeze portion within the chamber, opposing ends of the container including an opening and an outlet, respectively, the opening and the outlet being in communication with the chamber; and a sampling unit including a main body, the main body including a sample collection member which is made of deformable absorbent material, and a sealing portion, the sample collection member being insertable into the chamber and radially urging the squeeze portion, the sealing portion being annularly and sealingly engaged with an inner wall of the chamber.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

Figure 1:
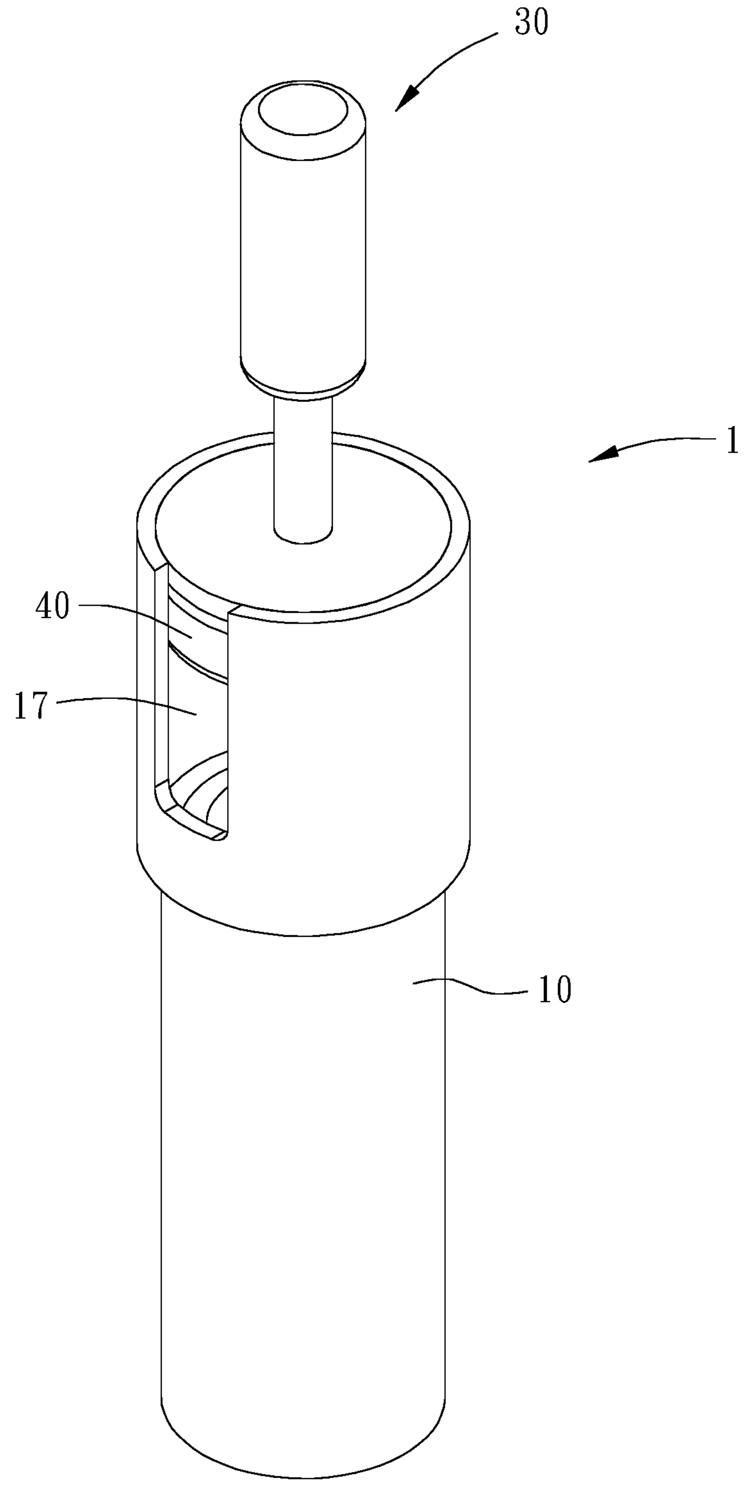
FIG. 1 is a stereogram of a first exemplary embodiment of the present invention.
Figure 2:
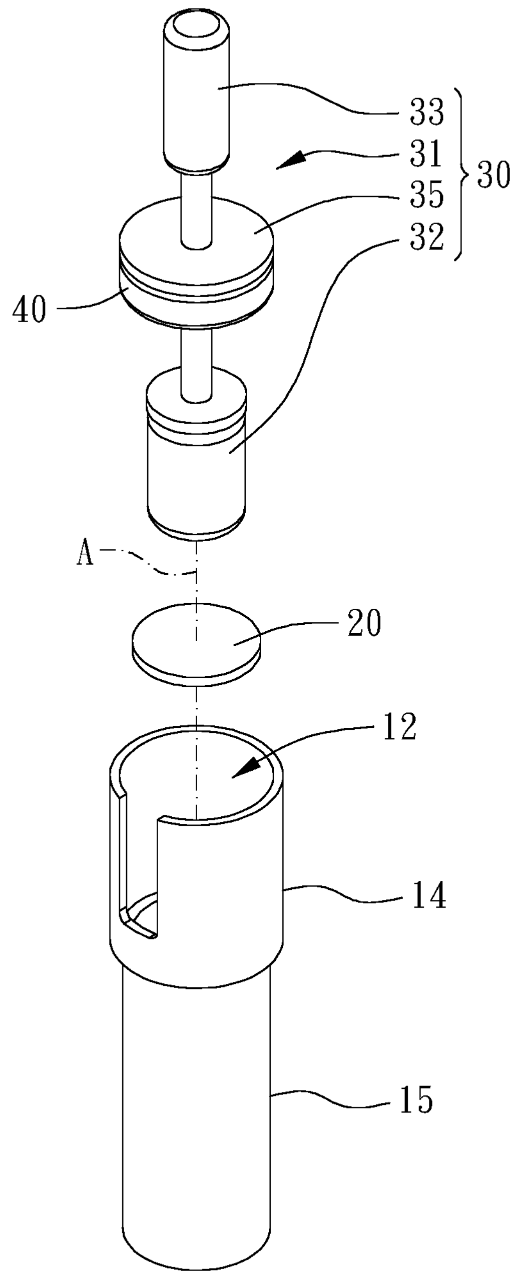
FIG. 2 is a breakdown drawing of the first exemplary embodiment of the present invention.
Figure 3:
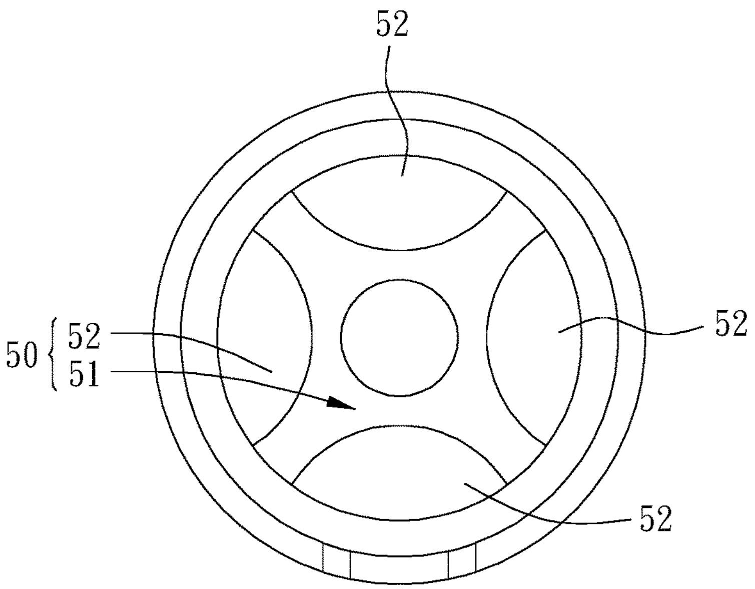
FIG. 3 is a top plan view of the first exemplary embodiment of the present invention.
Figure 4:
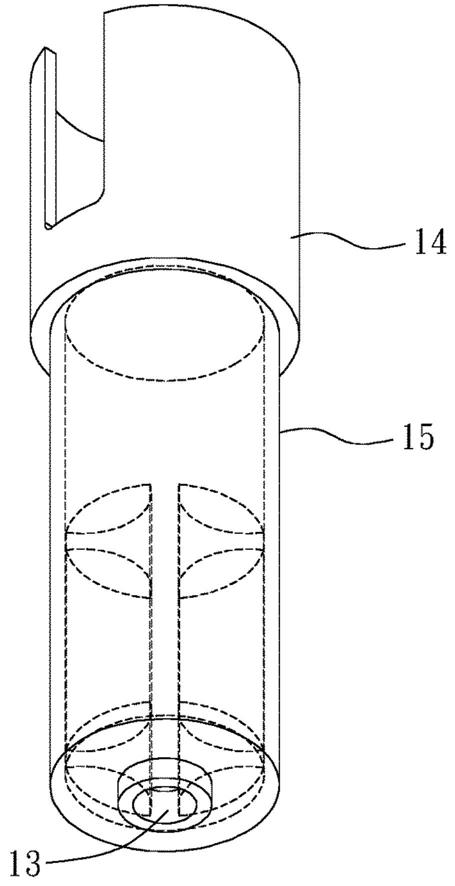
FIG. 4 is another stereogram of the first exemplary embodiment of the present invention.
Figure 5:
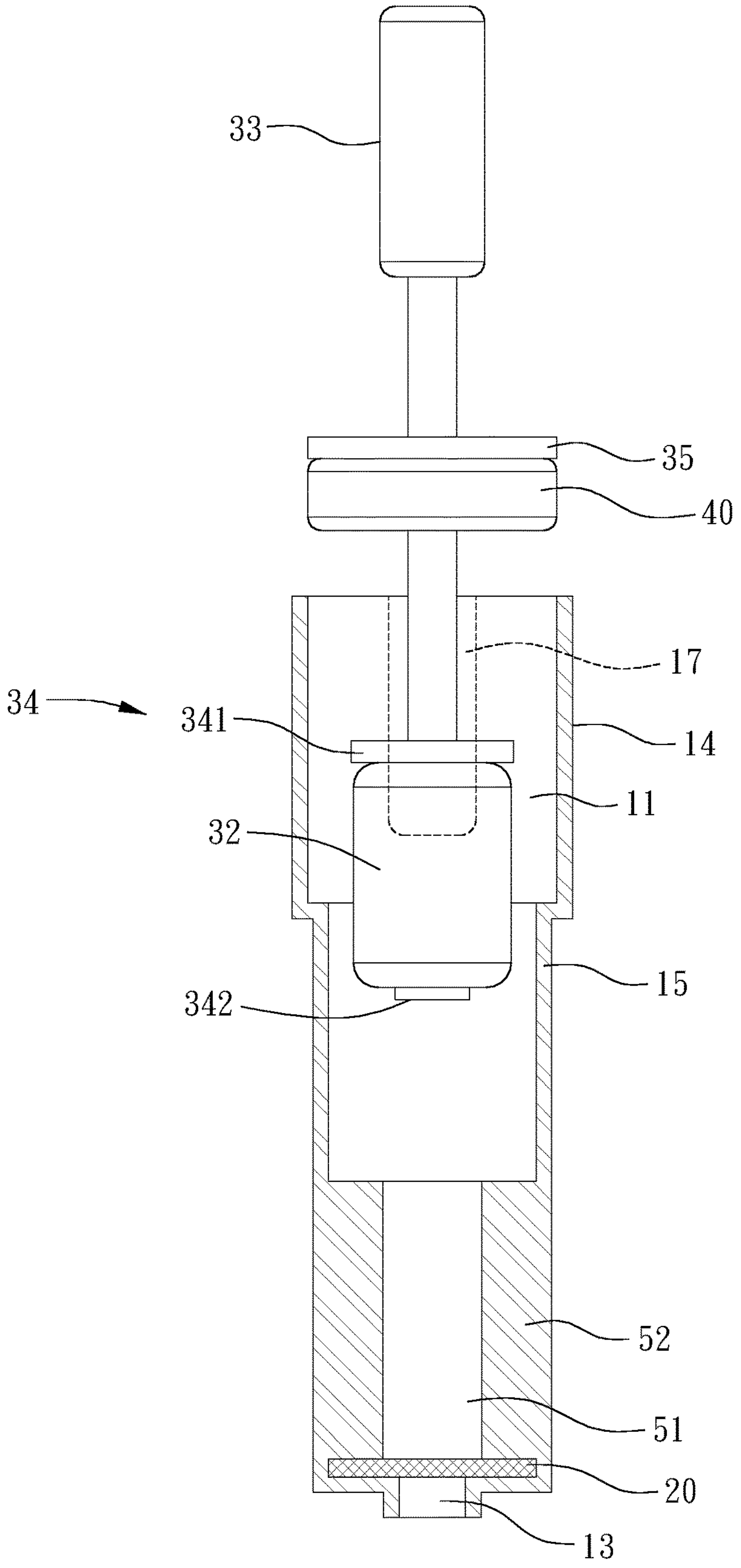
FIGS. 5-7 are drawings showing operation of the first exemplary embodiment of the present invention in use.
Figure 6:
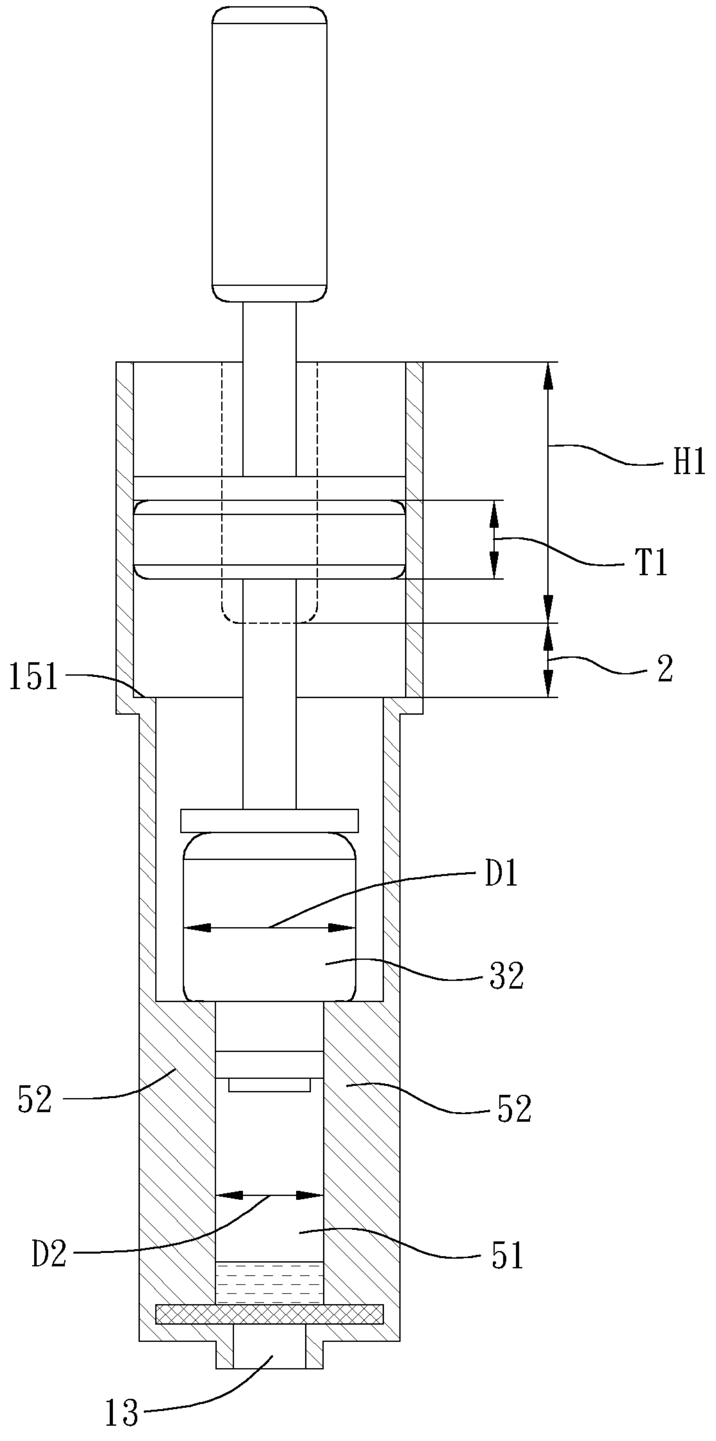

Please refer to FIGS. 1 to 7 for an exemplary embodiment of the present invention. A sample collection device 1 of the present invention includes a container 10 and a sampling unit 30.

The container 10 includes a chamber 11 and a squeeze portion 50 within the chamber 11, opposing ends of the container 10 includes an opening 12 and an outlet 13, respectively, and the opening 12 and the outlet 13 are in communication with the chamber 11. The sampling unit 30 includes a main body 31, and the main body 31 includes a sample collection member 32 which is made of deformable absorbent material, and a sealing portion 40. The sample collection member 32 is insertable into the chamber 11 and radially urges the squeeze portion 50, and the sealing portion 40 is annularly and sealingly engaged with an inner wall of the chamber 11 to block the flow of a fluid. The sample collection member 32 may be a sponge, a swab, or other materials capable of absorbing liquid. The sample collection member 30 can absorb a sample, such as saliva sample and other fluid sample, the sample collection member 32.

In use, the sample collection member 32 is used to collect a specimen, the specimen is squeezed out from the sample collection member 32, and the main body 31 is pushed to move the sealing portion 40 downward to press the specimen to come out from the outlet 13, which can carry out the collection of specimen and quantification precisely.

The sealing portion 40 is a rubber ring member (O-ring) so that the chamber 11 can be in a highly airtight. When the sealing portion 40 moves downward in the chamber 11, the air within the chamber 11 is compressed so that it prevents the specimen from flowing out backwards and adhering to the user's hands.

The squeeze portion 50 includes a channel 51 in communication with the outlet 13, and the sample collection member 32 has an outer diametric dimension D1 larger than a minimum outer diametric dimension D2 of the channel 51 so that the sample collection member 32 can be pressed into the channel 51, to discharge the specimen from the outlet 13, with the channel 51 entirely or partially sealed.

The container 10 further includes a through hole 17 in vicinity to the opening 12 and extending radially, the through hole 17 is in communication with the chamber 11, the main body 31 is configured to drive the sealing portion 40 to move axially in the chamber 11, the sealing portion 40 can pass over the through hole 17. The through hole 17 defines an axial dimension H1, and the sealing portion 40 has a thickness dimension T1 smaller than the axial dimension H1. In this embodiment, the thickness dimension T1 is smaller than 0.5 times of the axial dimension H1; the through hole 17 is open toward the opening 12; the chamber 11 will reach an airtight effect when the sealing member 40, which is disposed within the chamber 11, passes axially through the through hole 17 to be located beneath the through hole 17, so that the sealing member 40 can be tightly sealed with the container 10, and smoothly passed through the opening 12 into the chamber 11.

Figure 7:
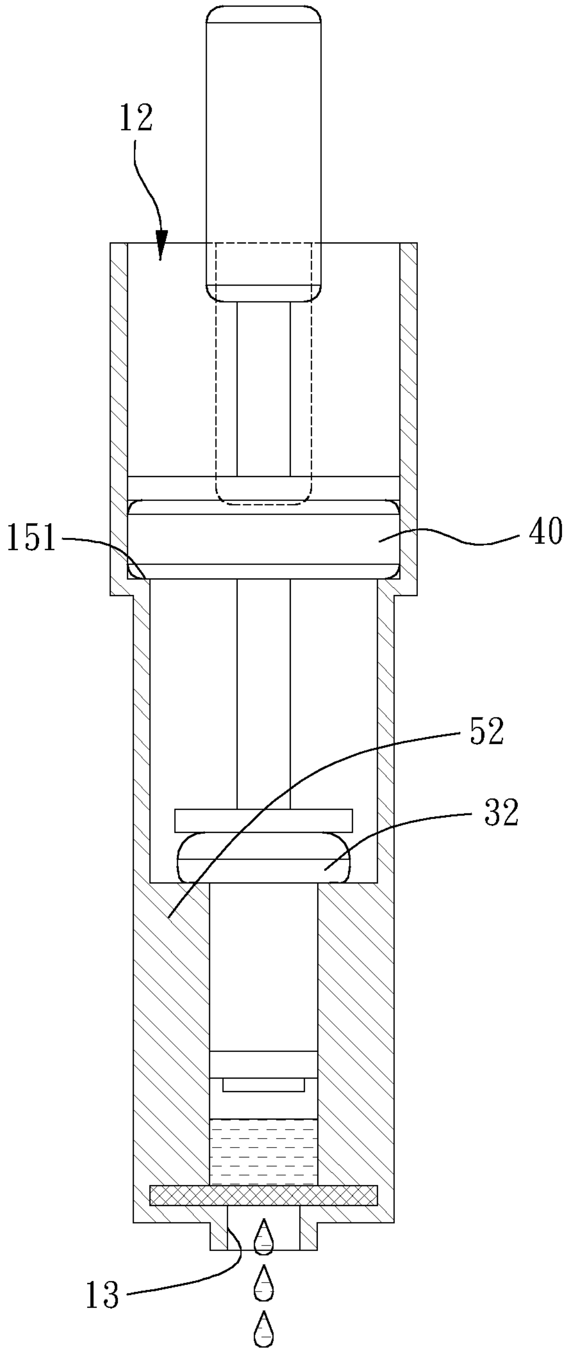

The container 10 further includes a blocking portion 151 projecting radially inward in the chamber 11, the blocking portion 151 and the through hole 17 are arranged in interval in an axial direction A, and the sealing portion 40 is radially abuttable against the blocking portion 151 in a direction away from the opening 12. In the axial direction A, a distance between the through hole 17 and the blocking portion 151 is defined as a travel distance 2, and the travel distance 2 is smaller than the axial dimension H1. As shown in FIG. 7, the travel distance of the sealing portion 40 in the chamber 11 can be limited, thus allowing the sealing member 40 to press a precisely quantified volume of the specimen through the outlet 13 during the pushing process.

The container 10 further includes a large diameter section 14 and a small diameter section 15 integrally connected to each other, the small diameter section 15 and the large diameter section 14 form the chamber 11, the small diameter section 15 includes the squeeze portion 50, the squeeze portion 50 includes a plurality of protrusions 52 projecting radially and arranged circumferentially, the plurality of protrusions 52 form the channel 51, and the plurality of protrusions 52 are configured to evenly squeeze the sample collection member 32. Preferably, the blocking portion 151 is formed between the large diameter section 14 and the small diameter section 15, the blocking portion 151 is stepped, an in the axial direction the blocking portion 151 is lower than the opening 12.

The sample collection device 1 further includes a filtration sheet 20, and the filtration sheet 20 is received in the small diameter section 15 and can be secured by the small diameter section 15. The impurities (such as food residue or other contaminants) from the specimen can be filtered by the filtration sheet 20.

The main body 31 includes a grip portion 33 and a connection portion 34 at opposing ends, respectively, the main body 31 further includes a cover portion 35 extending radially and located between the grip portion 33 and the connection portion 34, the sealing portion 40 is located between the cover portion 35 and the connection portion 34, and the cover portion 35 covers the opening 12, the sample collection member 32 is received in the connection portion 34, to provide multiple layers of protection. The specimen contained in the sample collection member 32 can be blocked by the cover portion 35 and the sealing portion 40 to prevent from splashing out of the opening 12 when the sample collection member 32 is squeezed by the plurality of protrusions 52. The grip portion 33 is configured for hand-holding to facilitate to stably insert the sample collection member 32 through the opening 12 into the chamber 11.

The connection portion 34 is I-shaped, the connection portion 34 includes a first flange 341 and a second flange 342 arranged in interval, and the sample collection member 32 is located between the first flange 341 and the second flange 342. Specifically, the sample collection member 32 is inserted in the connection portion 34 (rod-shaped), to limit the sample collection member 32 between the first flange 341 and the second flange 342.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A sample collection device including:

a container including a chamber and a squeeze portion within the chamber, opposing ends of the container including an opening and an outlet, respectively, the opening and the outlet being in communication with the chamber; and a sampling unit including a main body, the main body including a sample collection member which is made of deformable absorbent material, and a sealing portion, the sample collection member being insertable into the chamber and radially urging the squeeze portion, wherein the sealing portion is configured to be annularly and sealingly engaged with an inner wall of the chamber when the sample collection member is fully inserted into the container;

wherein the container further includes a through hole being adjacent to the opening and extending radially, the through hole is in communication with the chamber, the main body is configured to drive the sealing portion to move axially in the chamber, and the sealing portion can pass over the through hole;

wherein the container further includes a blocking portion projecting radially inward in the chamber, the blocking portion and the through hole are arranged in interval in an axial direction, and the sealing portion is radially abuttable against the blocking portion in a direction away from the opening;

wherein in the axial direction, a distance between the through hole and the blocking portion is defined as a travel distance, the through hole has an axial dimension, and the travel distance is smaller than the axial dimension.

2. The sample collection device of claim 1, wherein the squeeze portion includes a channel in communication with the outlet, and the sample collection member has an outer diametric dimension larger than an outer diametric dimension of the channel.

3. The sample collection device of claim 1, wherein the sealing portion has a thickness dimension smaller than the axial dimension of the through hole.

4. The sample collection device of claim 2, wherein the container further includes a large diameter section and a small diameter section integrally connected to each other, the small diameter section and the large diameter section form the chamber, the small diameter section includes the squeeze portion, the squeeze portion includes a plurality of protrusions projecting radially and arranged circumferentially, the plurality of protrusions form the channel, and the plurality of protrusions are configured to squeeze the sample collection member.

5. The sample collection device of claim 4, further including a filtration sheet, wherein the filtration sheet is received in the small diameter section.

6. The sample collection device of claim 1, wherein the main body includes a grip portion and a connection portion at opposing ends, respectively, the main body further includes a cover portion extending radially and located between the grip portion and the connection portion, the sealing portion is located between the cover portion and the connection portion, and the cover portion is configured to cover the opening, and the sample collection member is received the connection portion when the sample collection member is fully inserted into the container.

7. The sample collection device of claim 1, wherein the squeeze portion includes a channel in communication with the outlet, and the sample collection member has an outer diametric dimension larger than an outer diametric dimension of the channel; the sealing portion is a rubber ring member; the through hole is open toward the opening; the through hole has an axial dimension, and the sealing portion has a thickness dimension smaller than the axial dimension; the thickness dimension is smaller than 0.5 times of the axial dimension; the container further includes a large diameter section and a small diameter section integrally connected to each other, the small diameter section and the large diameter section form the chamber, the small diameter section includes the squeeze portion, the squeeze portion includes a plurality of protrusions projecting radially and arranged circumferentially, the plurality of protrusions form the channel, and the plurality of protrusions are configured to squeeze the sample collection member; the blocking portion is formed between the large diameter section and the small diameter section, the blocking portion is stepped, in the axial direction the blocking portion is lower than the opening; the sample collection device further includes a filtration sheet, and the filtration sheet is received in the small diameter section; the main body includes a grip portion and a connection portion at opposing ends, respectively, the main body further includes a cover portion extending radially and located between the grip portion and the connection portion, the sealing portion is located between the cover portion and the connection portion, and the cover portion is configured to cover the opening, and the sample collection member is received in the connection portion when the sample collection member is fully inserted into the container; the connection portion is I-shaped, the connection portion includes a first flange and a second flange arranged in interval, and the sample collection member is located between the first flange and the second flange.

* * * * *